United States Patent [19]

Sharma

[11] Patent Number: 5,171,662
[45] Date of Patent: Dec. 15, 1992

[54] METHOD OF DETECTING HIV PROTEASE ACTIVITY

[75] Inventor: Satish K. Sharma, Portage, Mich.

[73] Assignee: The Upjohn Company, Kalamazoo, Mich.

[21] Appl. No.: 680,679

[22] Filed: Apr. 4, 1991

Related U.S. Application Data

[63] Continuation-in-part of Ser. No. 581,715, Sep. 13, 1990, abandoned.

[51] Int. Cl.$^5$ .......................... G01N 33/50; C12Q 1/00
[52] U.S. Cl. .......................................... 435/5; 435/7.1; 435/7.92; 435/23; 435/24; 435/974
[58] Field of Search .......................... 435/5, 7.1, 23, 24, 435/7.92

[56] References Cited

U.S. PATENT DOCUMENTS

| | | | |
|---|---|---|---|
| 4,918,001 | 4/1990 | Kolde | 435/24 |
| 4,952,493 | 8/1990 | Kettner et al. | 435/5 |
| 5,011,910 | 4/1991 | Marshall et al. | 530/329 |

OTHER PUBLICATIONS

Bu, Ming et al. "Inhibition of Bacterially Expressed HIV Protease Activity Determined by an In Vitro Cleavage Assay with MuLV Pr65$^{gag}$". AIDS Research and Human Retroviruses. 5(3)1989, 259–268.

Evans, D. B., et al., "Substrate Specificity and Inhibitor Structure-Activity Relationships of Recombinant Human Renin: Implications in the in Vivo Evaluation of Renin Inhibitors," (1990), Biotechnol. Appl. Biochem. 12:161–175.

Gottfried, T. D. and H. B. Urnovitz, "HIV-1 Testing: Product Development Strategies," (1990), Tibtech 8:35–40.

D. P. Bolognesi, "Approaches to HIV Vaccine Design," (1990), Tibtech 8:40–45.

Cornette, J. C., et al., "Renin Activity Determination Using Human Plasma as a Substrate," (1987), Analyt. Biochem., 163:93–99.

Sharma, S. K., et al., "A Primate Bioassay for the Determination of Renin Inhibitory Peptides in Serum," (1990), Analyt. Biochem., 186:24–27.

"GammaCoat TM [$^{125}$I] Plasma Renin Activity Radioimmunoassay Kit," Baxter Cat. Nos. CA-533-553.

Wondrak, E. M., et al., "A Solid Phase Assay for the Protease of Human Immunodeficiency Virus," (1990), Analyt. Biochem., 188:82–85.

Hansen, J., et al., "Partial Purification and Substrate Analysis of Bacterially Expressed HIV Protease by Means of Monoclonal Antibody," (1988), The EMBO Journal, 6:1785–1791.

Giam, C-Z and I. Boros, "In Vivo and In Vitro Autoprocessing of Human Immunodeficiency Virus Protease Expressed in *Escherichia coli*," (1988), J. Biol. Chem., 263:14617–14620.

Nutt, R. F., et al., "Chemical Synthesis and Enzymatic Activity of a 99-Residue Peptide With a Sequence Proposed for the Human Immunodeficiency Virus Protease," (1988), Proc. Natl. Acad. Sci. USA, 85:7129–7133.

Kräusslich, H-G, et al., "Processing of In-Vitro-Synthesized gag Precursor Proteins of Human Immunodeficiency Virus (HIV) Type 1 by HIV Proteinase Generated in *Escherichia coli*," (1988), J. of Virology, 62:4393–4397.

Louis, J. M., et al., "Chemical Synthesis and Expression of the HIV-1 Protease Gene in *E. Coli*," (1989), Biochem. & Biophys. Res. Comm., 159:87–94.

Moore, M. L., et al., "Peptide Substrates and Inhibitors of the HIV-1 Protease," (1989), 159:420–425.

Vlasuk, G. P., et al., "Purification and Characterization of Human Immunodeficiency Virus (HIV) Core Precursor (p55) Expressed in *Saccharomyces cerevisiae*," (1989), 264:12106–12112.

Blumenstein, J. J., et al., "Synthetic Non-Peptide Inhibitors of HIV Protease," (1989), Biochem. & Biophys. Res. Comm., 163:980–987.

*Primary Examiner*—Christine M. Nucker
*Assistant Examiner*—Chris Dubrule
*Attorney, Agent, or Firm*—Mark DeLuca

[57] ABSTRACT

A method for identifying compounds that inhibit HIV protease is disclosed. A substrate that comprises an HIV protease cleavage site is combined with HIV protease and test compounds. Cleavage of the substrate indicates protease activity and can be detected using antibodies against a cleavage product which do not cross react with uncleaved substrate. A method of detecting the presence of anti-HIV protease antibodies in a sample is also disclosed. A substrate is combined with the sample and HIV protease. Detection of substrate cleavage indicates that the protease is active and that there is an absence of neutralizing anti-HIV protease antibodies.

22 Claims, No Drawings

METHOD OF DETECTING HIV PROTEASE ACTIVITY

CROSS REFERENCE TO RELATED APPLICATIONS

This application is a continuation-in-part of U.S. application Ser. No. 07/581,715, filed Sep. 13, 1990, which is abandoned.

FIELD OF THE INVENTION

The present invention relates to a peptide substrate that contains an amino acid sequence capable of being cleaved by HIV protease and that can be distinguished from the fragments generated by protease cleavage of the substrate. The present invention relates to a method of identifying compounds useful as HIV protease inhibitors in vitro and in bioassays and to a method of detecting the presence of antibodies against HIV protease in biofluids of patients.

BACKGROUND OF THE INVENTION

The human immunodeficiency virus (HIV) is recognized to be the agent resposible for acquired immunodeficiency disease syndrome (AIDS). HIV is a lentivirus. The processing of HIV-fusion polypeptides, the products of the gag and pol genes of HIV, is carried out by a virally-encoded protease. This processing has been demonstrated to be crucial to the replication of both HIV type-1 (HIV-1) and HIV type-2 (HIV-2), collectively referred to herein as HIV.

Inhibition of the viral protease and search for its inhibitors have been the subjects of immense interest for the last few years. Kinetic assays for HIV protease include HPLC assays, cleavage of a radiolabeled decapeptide, and spectrophotometric assays utilizing chromogenic and fluorogeneic substrates. HPLC assays, compared with spectrophotometric assays, are time-consuming and discontinuous. Other assay techniques are cumbersome and require synthesis of appropriate substrates. Conventional wisdom dictates that none of these assays would allow high-volume evaluation of protease inhibitors in animal models.

There is a need for a rapid, sensitive, generic, and high volume assay for the HIV protease for in vitro screening as well as for tracking its inhibitors in the blood in common laboratory animals. Therefore, it is conceived that if, in fact, one could find a substrate for the HIV protease that can be cleaved by the protease to produce a target for specific antibodies that will not cross react with the uncleaved substrate, such a system would be valuable for testing HIV protease inhibitors in animal models and in humans.

In addition, there is a need for sensitive, i.e, accurate and precise, diagnostic kits to determine whether or not a patient has been exposed to HIV. The most common method currently being exploited is the use of anti-HIV antibody immunoassay kits. While these kits are easy to use and relatively inexpensive, there is a great concern about the high number of false positives inherent in such methodology. Alternatively, a sample taken from a patient is prepared and separated on a Western blot to visually identify the presence of HIV protease using anti-HIV antibodies. This methodology, although very accurate, is time consuming and expensive. There is a need for a simple, inexpensive and highly sensitive method to detect the presence of antibodies to HIV proteins.

The present invention relates to a peptide substrate that contains an amino acid sequence capable of being cleaved by HIV protease and that can be distinguished from the fragments generated by protease cleavage of the substrate. The substrates of the present invention are useful in the screening and study of compounds which inhibit HIV protease and in diagnostic kits to detect the presence of antibodies against HIV protease.

The present invention provides an assay of identifying compounds useful as HIV protease inhibitors which can be used to investigate compounds in vitro or from fluids taken from patients. By providing a substrate comprising an HIV protease cleavage site and by having the ability to distinguish cleaved product from uncleaved substrate, the present invention provides a method of testing the inhibitory activity of compounds. The present invention provides a system for high volume screening of compounds which is used to identify those compounds useful as HIV protease inhibitors. The same system is particularly useful in bioassays to track activity of inhibitor compounds in vivo. There is a need for an easy and inexpensive diagnostic test system which can detect the presence of antibodies against HIV proteins accurately. Therefore, it is conceived that if one could find a substrate for the HIV protease that can be cleaved by the protease to produce a target for specific antibodies that will not cross react with the uncleaved substrate, such a system would be valuable for detecting the presence of antibodies against HIV protease in a biofluid sample.

The present invention provides an assay for identifying the presence of antibodies to HIV protease in fluids taken from patients; such an assay being used to diagnose HIV infection. By combining an HIV protease cleavage site on a substrate with the ability to distinguish cleaved product from uncleaved substrate, the present invention provides the ability to detect the presence of antibodies against HIV protease. The present invention provides a system for accurate detection of antibodies against HIV protease simply and inexpensively.

INFORMATION DISCLOSURE

Evans, D. B., et al., Biotechnol. Appl. Biochem. 12:161-175, 1990, relate to substrate specificity of renin from various species. Plasma angiotensinogens from human, monkey, baboon, rat, pig, rabbit, hamster, and dog were exposed to human renin and the activity of human renin for converting the angiotensinogen into Angiotensin I (Ang I) for the various species was determined. The substrate specificity was studied with respect to variations in the renin cleavage site.

Gottfried, T. D. and H. B. Urnovitz, Tibtech 8:35-40, February 1990, refer to product development strategies for HIV testing. A review is provided of the various diagnostic tests currently available to detect HIV infection in humans and in blood. A discussion of the strategies used in various diagnostic kits is provided.

Bolognesi, D. P., Tibtech 8:40-45, February 1990, refers to approaches to HIV vaccine design. Background material includes a description of HIV and discussion of strategies in vaccine design is provided.

Cornette, J. C., et al., Analyt. Biochem. 163:93-99, 1987, describe a renin activity assay. A method is disclosed which demonstrates that human renin activity can be determined using blood plasma as a substrate.

The blood plasma is converted to Ang I when incubated with active human renin. A commercially available radio-immunoassay for Ang I can be used to detect the presence of Ang I; detection of Ang I indicates the human renin is active. Thus, a conversion from a non-detectable protein, angiotensinogen, to a detectable protein, Ang I, allows for the study of the activity of the enzyme human renin.

Sharma, S. K., et al., Analyt. Biochem. 186:24–27, 1990, refer to a primate bioassay for the determination of renin inhibitory peptides in serum. A bioassay is described which is valuable in monitoring serum levels of thermostable renin inhibitory peptides from pharmacokinetic, bioavailability, and pharmacodynamic studies in primates. The procedure involves the inactivation of monkey angiotensinogen and monkey renin by thermal denaturation prior to analysis. The denaturized monkey serum is mixed with renin inhibitory peptides and the mixture is exposed to angiotensinogen and active human renin. If the renin inhibitory peptide mixed with the monkey serum is capable of inactivating the added human renin, the added angiotensinogen I will not be converted to Ang I. Accordingly, antibodies against Ang I will not detect its presence. If, however, the renin inhibitory peptide does not effectively inhibit renin activity, the angiotensinogen I will be converted to Ang I and detected by anti-Ang I antibodies.

Baxter Cat. Nos. CA-533-553, describes a commercially available Plasma Renin Activity Radioimmunoassay Kit. In the kit anti-Ang I antibodies are attached to the inner wall of a tube. Initial incubation of a plasma with renin substrate will generate Ang I from the renin substrate if renin is active. The detection of Ang I is made and quantitated with the radioimmunoassay for Ang I.

Wondrak, E. M., et al., Analytical Biochem. 188, 82-85 (1990) disclose a solid phase assay for HIV protease using an immobilized substrate modeled after the p17/p14 cleavage site of HIV. The substrate is immobilized at the N-terminal and the carboxy terminal is radiolabeled. Cleavage at the HIV protease cleavage frees the radiolabel and HIV protease activity can be determined accordingly. This reference was published after the date of the invention and is not considered prior art.

Bu, M., et al., Aids Research and Human Retroviruses, Vol. 5, No. 3 pp. 259-268 (1989) disclose using HIV precursor polyproteins as substrates to detect HIV protease activity. Conversion of the polyprotein into subunit proteins by HIV cleavage is detected by immunoblotting.

Hanse, J., et al., The Embo Journal, Vol. 7, No. 6, pp. 1785-1791 (1988) disclose the cleavage of HIV gag precursor polyproteins to substituent proteins by HIV protease. This cleavage can be inhibited by pepstatin A. However, modification of the portion of the gene that codes for the region of the polyprotein which contains the protease cleavage site produces a polyprotein that cannot be cut by the protease.

Giam, C. Z. and Boros, I., J. Biol. Chem., Vol. 263, No. 29, pp. 14617-14620 (1988) disclose detecting protease cleavage activity by the autoprocessing of the HIV protease from a precursor protein containing the protease and portions of the gag protein and reverse transcription protein including protease cleavage sites at each junction. The autoprocessing which liberates the protease from the precursor can be inhibited by the use of alkaline buffers or pepstatin A. Detection of the protease liberated from the precursor is accomplished by using antisera prepared against the putative protease sequence.

Nutt, R. F., et al., Proc. Natl. Acad. Sci. USA, Vol. 85, pp. 7129-7133 (October 1988) disclose the chemical synthesis and enzymatic activity of a 99-residue peptide with the sequence proposed for the HIV protease. Activity of the 99-residue peptide is demonstrated by cleaving the natural substrate gag protein p55 into gag p24 and gag p17. The proteolytic action of the synthetic protease can be inhibited by pepstatin.

Kräusslich, H. G., et al., J. of Virology, No. 1988, pp. 4393-4397 disclose processing of in vitro synthesized gag precursor protein of HIV-type 1 by HIV protease generated in E. coli. Processing the of gag precursor protein containing naturally occurring HIV protease cleavage site was detected using immunodetection of the products.

Louis, J. M., et al., Biochem. & Biophys. Res. Comm., Vol. 159, No. 1, pp. 87-94 (1989) refer to chemical synthesis and expression of the HIV 1 protease gene in E. coli. To measure the activity of the protease being synthesized a synthetic nonapeptide spanning the cleavage site between p17-p24 in the gag polypeptide was used. Detection of the conversion of the nonapeptide into two cleavage products was determined by separating the materials with reverse high phase liquid chromatography.

Moore, Michael L., et al., Biochem. & Biophys. Res. Comm., Vol. 159, No. 2, pp. 420-425 Mar. 15, 1989) refer to peptide substrates that are inhibitors of HIV protease. Minimum substrate size is described using heptapeptide design upon the gag protease cleavage sequence. Using substrates described, it is suggested that inhibitors of HIV protease may be identified.

Vlasuk, G. P., et al., The J. of Biol. Chem., Vol. 264, No. 20, pp. 12106-12112 Jul. 15, 1989) relate to the purification of HIV precursor p55 in yeast. Proteolytic cleavage of the recombinant protein by HIV protease yielded substituent proteins of the polyprotein.

Blumenstein, J. J., et al., Biochem. & Biophys. Res. Comm., Vol. 163, No. 2 pp. 980-987 (1989) disclose a synthetic nonapeptide inhibitor of HIV protease which was studied by monitoring the cleavage of an authentic single peptide bond and a synthetic nonapeptide corresponding to natural cleavage site of HIV gag precursor polyprotein. The cleavage site of the synthetic nonapeptide is modeled after the HIV cleavage site between p17 and p24. Protease cleavage activity was monitored by HPLC and expressed as the amount of pentapeptide cleavage product produced relative to an uninhibited control.

SUMMARY OF THE INVENTION

The present invention relates to a method of identifying compounds that inhibit HIV protease. According to the present invention, a substrate that comprises an HIV protease cleavage site is combined with HIV protease and test compounds. Cleavage of the substrate can be detected using antibodies against Ang 1 which cross react with one of the cleavage products. Detection of substrate cleavage indicates protease activity while impaired activity suggests that the test compound affects the protease as an inhibitor. The present invention also relates to a method of detecting the presence of anti-HIV protease antibodies in a sample. According to the present invention, the substrate is combined with the sample and HIV protease. Detection of substrate cleavage indicates protease activity and the absence of neutralizing anti-HIV protease antibodies.

DETAILED DESCRIPTION OF THE INVENTION

The present invention provides substrates that contain amino acid sequences which can be cleaved by HIV protease. Protein substrates which comprise the protease cleavage sites of the present invention can be used in cooperation with immunoassay technology or other standard detection methodology in a system that can distinguish cleaved and uncleaved substrate, thus detect the presence of HIV protease activity. The ability to detect the presence of HIV protease activity is useful in systems to identify compounds which effect the activity of HIV protease or to determine the presence of antibodies against HIV protease.

The substrate must have three characteristics to be useful in the present invention. First, it must contain an HIV protease cleavage site. As used herein, the term "protease cleavage site" refers to an amino acid sequence comprising eight amino acids which can be cleaved by HIV protease at a scissile bond. Second, when cleaved by the HIV protease, the substrate must be converted into at least two separate cleavage products, at least one of which will bind to anti-Ang I antibodies. Third, the anti-Ang I antibodies must not cross react with uncleaved substrate because there must be a means to distinguish the uncleaved substrate from at least one cleavage product so that cleavage can be determined. Thus, anti-Ang I antibodies are used to determine whether or not the substrate has been cleaved by detecting the presence of the cleavage product. As used herein, the term "anti-Ang I antibodies" refers to any antibody which binds to the amino acid sequence Asp-Arg-Val-Tyr-Ile-His-Pro-Phe-His-Leu including antibodies which additionally recognize similar sequences.

According to the prior art, the HIV protease is a very nonspecific enzyme that cleaves at amino acid sequences which are not easily predicted. Cleavage of the Ang I precursor substrate by HIV protease was surprising and highly unpredictable. In addition to discovering HIV protease cleaves the Ang I substrate, statistical analysis of an expanded database of regions in viral polyproteins and in non-viral proteins that are sensitive to hydrolysis by the protease from HIV-1 has generated a model which characterizes the substrate specificity of this retroviral enzyme. The model leads to an algorithm for predicting protease-susceptible sites from the primary structure. According to the present invention, substrates that are cleavable by HIV protease can be predicted using an algorithm that assigns specific numerical values to each of the twenty known amino acid residues for each of eight positions which make up the protease cleavage site. The eight positions which comprise the scissile bond include four amino acids N-terminal to the bond and four amino acids C-terminal to it. The protease cleavage site of a substrate according to the present invention is represented by the formula $$P_4-P_3-P_2-P_1-P_1'-P_2'-P_3'-P_4'$$

wherein going left to right ($P_4$ to $P'_4$) represents going from the amino terminus to the carboxy terminus. The HIV protease cuts this sequence between $P_1$ and $P_1'$, the scissile bond. The algorithm can be expressed as follows:

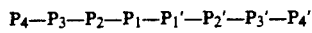

$$h = \frac{RP}{RP - 166}$$

wherein h is the probability of cleavage by HIV protease, and RP is the product of multiplying the numerical values assigned to each of the eight positions of the sequence, the numeric values being determined based on the specific amino acid occupying a particular position. Table I provides the eight numerical values accorded to each of the twenty amino acids for each of the eight positions in the HIV-1 protease cleavage site. Table II provides the eight numerical values accorded to each of the twenty amino acids for each of the eight positions in the HIV-2 protease cleavage site. It has been determined that when h is greater than 0.13 the protease of the HIV type of whichever table is used to determine h will cleave the sequence at the scissile bond.

In the present invention, the substrate is preferably about 14 amino acids long and the HIV protease cleavage site is only cleavable by HIV protease. In the most preferred embodiment, the peptide is cleaved between amino acids 10 and 11. The preferred sequences which make up the protease cleavage site are Pro-Phe-His-Leu-Leu-Val-Tyr-Ser, Pro-Phe-His-Leu-Leu-Glu-Ile-Ser or Pro-Phe-His-Leu-Leu-Glu-Glu-Ser. The preferred substrate is Asp-Arg-Val-Tyr-Ile-His-Pro-Phe-His-Leu-Leu-Val-Tyr-Ser.

The second and third characteristics of a substrate according to the present invention are related. They require that the substrate be converted into at least two separate cleavage products; one of which will bind with anti-Ang I antibodies that do not cross react with the uncleaved substrate. Thus, when a substrate is cleaved by the HIV protease, the cleavage products can be distinguished from the uncleaved substrate using anti-Ang I antibodies. According to the present invention, a substrate is cleaved and at least two fragments are generated; at least one of which can be recognized by an anti-Ang I antibody. As used hereinafter, the term "reactive cleavage product" refers to a peptide fragment generated by cleavage of the substrate which can form complexes with anti-Ang I antibodies. Thus, to practice the present invention, the anti-Ang I antibodies that bind to a cleavage generated fragment must not cross react with the substrate.

Such antibodies can be made by one having ordinary skill in the art using standard techniques. Methods of production and use of antibodies, both polyclonal and monoclonal are widely known and practiced. Briefly, to make antibodies, a sample of the reactive cleavage product is injected into a laboratory animal. Polyclonal antibodies against the fragment can be isolated from serum. Alternatively, using hybridoma technology, monoclonal antibodies may be produced against the antigen. In the preferred embodiments, antibodies are bound to a radiolabelled ligand.

According to the present invention, antibodies used against reaction products must not cross-react to the uncleaved substrate. The antibodies are used to indicate whether the HIV protease activity has been hindered by determining whether or not the substrate has been cleaved. Thus, when practicing one embodiment of the present invention, HIV protease, a substrate and a compound being tested are combined. After a sufficient reaction time, anti-Ang I antibodies are added. If antibodies bind to a reactive cleavage product, the protease will have cleaved the substrate. If the substrate has not been cleaved, the antibody cannot react and inhibition of the protease by the compound being tested is indicated. In the preferred embodiment, the substrate is a tetradecapeptide that is a precursor for the reactive cleavage product Ang I. The substrate cannot cross-react with the anti-Ang I antibodies.

The protease used in the present invention can be derived from HIV-1 or HIV-2. HIV-1 protease is available commercially. HIV-2 protease can be produced from readily available starting materials using techniques well known in the art.

To practice one aspect of the present invention, the substrate, HIV protease and compound being tested are combined in an in vitro assay or in a bioassay in which the compound is mixed with animal biofluid or the compound is contained in serum extracted from an animal exposed to the compound. In the case of a compound mixed with biofluid, such a mixture is referred to as a spiked sample which means mixing a compound with biofluid that was extracted from an animal not exposed to the compound. Using spiked sample allows the testing of the compound's activity in the presence of bodily fluids. Alternatively, the compound may be administered to an animal, for example orally or by intravenous, intramuscular, intraperitoneal or subcutaneous injection. Biofluid can then be extracted from various parts of the animal to allow pharmacokinetic properties of the compound to be studied. Absorption, disposition, metabolism and elimination (ADME) profiles of compounds can be studied using the method taught here. In addition, the stability of the compound's activity can be determined.

The standard in vitro test can be performed using 1-2 $\mu$M substrate, 5-50 nM active HIV protease, and 5-1000 nM of HIV protease inhibitor. The product of reaction can be measured by using an immunoassay based on polyclonal or monoclonal antibodies to the product of interest. There are several variations of immunoassay techniques. The preferred method according to the present invention is the competitive binding principles of radioimmunoassay (Yalow, R. S., Berson, S. A., in Principles of competitive protein binding assays, Odell and Daughaday (eds.), Lippincott, Philadelphia, Ch 1, 1971). In this case the antibody is immobilized onto the lower inner wall of the plastic test tube. The antibody titer as defined by $\mu$g immobilized per tube is 0.1 to 0.9 $\mu$g/tube from a "GammaCoat" Plasma Renin Activity Radioimmunoassay kit. The reaction product is allowed to compete for these antibodies in the presence of labeled antigen. Methods for the incorporation of radiolabel into purified antigen are well known.

Using compounds spiked with biofluid, the test is performed using 1-2 $\mu$M substrate, 5-50 nM active HIV protease, and 5-1000 nM of HIV protease inhibitor. The inhibition of reaction product is quantitated by an immunoassay based on antibodies to the reaction product, as described above.

Biofluid can be obtained from the blood, tissue, and organs of animals administered the compound. The test can be performed using 1-2 $\mu$M substrate, 5-50 nM active HIV protease, and 0.5-1000 nM of HIV protease inhibitors. The product inhibition is measured by an immunoassay based on antibodies to the reaction product, as described above.

In another embodiment of the present invention, the substrate may be used in a diagnostic test kit to detect the presence of antibodies against the HIV protease as an indication of HIV infection. Employing this embodiment, biofluid from a subject is combined with the protease and the substrate. The mixture is subsequently exposed to antibodies against the reactive cleavage product to detect whether or not the substrate has been cleaved. If the substrate has not been cleaved, the presence of antibodies against HIV protease in the sample is indicated which suggests that the patient supplying the sample has been infected with HIV.

The standard HIV diagnostic test can be performed using 1-2 $\mu$M substrate, 0.1-1 $\mu$g/ml active HIV protease, and sera from the blood of a patient. Determination of whether the substrate has been cleaved can be measured by using an immunoassay based on polyclonal or monoclonal antibodies. There are several variations of immunoassay techniques. The preferred method according to the present invention is the competitive binding principles of radioimmunoassay (Yalow, R. S., Berson, S. A., in Principles of competitive protein binding assays, Odell and Daughaday (eds.), Lippincott, Philadelphia, Ch 1, 1971). In this case the antibody is immobilized onto the lower inner wall of a plastic test tube from a "GammaCoat" Plasma Renin Activity Radioimmunoassay kit. The antibody titer as defined by $\mu$g/ng immobilized per tube is 0.1 to 0.9 $\mu$g/tube. The reaction product is allowed to compete for these antibodies in the presence of labeled antigen. Methods for the incorporation of radiolabel into purified antigen are widely known.

The present invention and contemplated equivalents thereof include substrates which when exposed to HIV protease are converted into cleavage products and either the substrates or the cleavage products are detectable but not both. Contemplated equivalents include substrates which can be detected by antibodies that do not cross react with cleavage products and methods which employ such substrates. The present invention and contemplated equivalents thereof include substrates and/or cleavage products which are detectable by means other than antibodies, for examples those which are detectable by their reaction with other components to form detectable products. One such embodiment would be a substrate that is an enzyme which functions in a biological reaction; the reaction being detectable. If cleaved by an HIV protease, the enzyme would be rendered non-functional. Alternatively, the enzyme can be a cleavage product which is only functional if the HIV protease cleaves the non-functioning substrate. Essential elements of the present invention include a substrate which is converted by HIV protease cleavage into at least one cleavage product in which the substrate and/or at least one of the cleavage products are distinguishable from each other.

EXAMPLE 1

Production of Ang I and its determination by Ang I RIA in TDP-HIV Protease System The tetradecapeptide (TDP) substrate, Asp-Arg-Val-Tyr-Ile-His-Pro-Phe-His-Leu-Leu-Val-Tyr-Ser, was obtained from Peninsula Laboratories, Inc., Belmont, Calif. The Ang I RIA kit was purchased from Baxter Health Care Corporation, Cambridge, Mass. Recombinant HIV-1 protease was purified and refolded from *E. coli* as published previously (Tomasselli, A. G. et. al. (1990) Biochemistry 29, 264-269). The TDP substrate has an HIV protease cleavage site which when cut at the Leu-Leu bond produces authentic Ang I. The Ang I RIA kit detected the Angiotesin I if produced.

The protease cleavage site of the TDP is Pro-Phe-His-Leu-Leu-Val-Tyr-Ser. The probability, h, can be determined as follows. First, using Table I, the numerical values for the amino acid residues of the protease cleavage site are determined. According to Table I, Pro in position $P_4$ is 2.22, Phe in position $P_3$ is 1.92, His in position $P_2$ is 1.14, Leu in position P is 3.66, Leu in position $P'_1$ is 0.91, Val in position $P'_2$ is 1.43, Tyr in position $P'_3$ is 0.76, and Ser in position $P'_4$ is 1.89. The sum of these values, $2.22 \times 1.92 \times 1.14 \times 3.66 \times 0.91 \times 1.43 \times 0.76 \times 1.89$ represent RP. Thus RP is 33.24. Using the algorithm h is determined.

$$h = \frac{33.24}{33.24 + 166} = 0.166$$

Thus h=0.17. According to the model since h is greater than 0.13 the substrate will be cleaved by HIV-1 protease between the Leu-Leu bond.

The various steps of the in vitro assay to screen a compound were performed as follows. The series of assays are done for each compound, each assay using a different concentration of compound. The various reagents were added to the system in the order which they are listed.

1. 52 μl assay buffer (0.1M Sodium Acetate, 10% glycerol, 3 mM EDTA, 5% ethylene glycol, 1 mg/ml BSA, pH 5.5)
2. 15 μl HIV-1 protease (final Concentration in assay 0.75 μg/ml). For inhibition studies, 12 μl of inhibitor solution was added prior to adding the enzyme.
3. 135 μl of 2.8 uM substrate (final concentration about 1.9 μM)
4. Incubate mixture for 1 hr, 37° C., boil for 5 min, and spin for 3 min at 10,000 rpm.
5. Dilute supernatant 1:10 in assay buffer and 100 μl was added to a rabbit anti-angiotensin I serum-coated from a "GammaCoat" Plasma Renin Activity Radioimmunoassay kit tube and mixed immediately with 1 ml of $^{125}$I-labeled Angiotensin I tracer reagent. Radioactive Angiotensin I is allowed to compete with the Angiotensin I of unknowns or standards for binding to the antibody coated tubes. Following an overnight equilibration at room temperature, the tubes are drained and the amount of radioactivity ($^{125}$I-labeled Ang I) remaining on the tube is determined in a gamma counter. The Ang I standard is run in duplicate each time the assay is run for the unknowns which are also are run in duplicate. Inhibition of HIV-1 protease activity is expressed in terms of nanograms of Ang I per ml per hr at 37° C. Controls include assay runs with no inhibitor and with no HIV-1 protease.

EXAMPLE 2

For in-vitro studies (described in Example 1 above) the compounds were dissolved in DMSO to a concentration of $10^{-4}$M. These samples were then diluted in DMSO to the appropriate concentrations and aliquot were used in the in-vitro assays and the standard curves described below.

For spiking studies, the stock solution described above were spiked directly into freshly drawn whole rat blood to a concentration of $8.25 \times 10^{-6}$M. Blood was allowed to clot and the serum was removed after centrifugation of the blood at 3,000 rpm for 30 min. Samples were diluted in normal rat serum to the appropriate concentrations and aliquots were assayed as described in Example 1.

EXAMPLE 3

Pharmacokinetic Studies of HIV Protease Inhibitors

For pharmacokinetic studies, the compound is dissolved in appropriate buffer between 0.2 mg/ml and 2.25 mg/ml. 1 ml of each of the above solutions is injected per rat. Male, Charles River, Sprague Dawley rats were fasted overnight in home cages with water available ad lib. Animals were anesthetized with diolurethane then administered the compound under ADME study at 10 mg/kg or at 1 mg/kg, intravenously and/or by other routes. Blood was then sampled from the orbital sinus at 0 (predose), 1, 10, 30, 60, 120 min. Blood was allowed to clot and the serum was collected and assayed as described in Example 1. Likewise, bile and urine were collected at various time points after dosing and assayed for the presence of the compound by following inhibition of HIV protease activity as described in Example 1.

A slightly modified version of the above in-vitro assay was used to determine the serum concentration of the various compounds in rats. Samples were analyzed as follows:

1. 40 μl Assay Buffer
2. 12 μl Rat serum
3. Boiled 5 min. (to eliminate rat renin activity)
4. 15 μl HIV protease (0.75 μg/ml final concentration)
5. 135 μl TDP substrate (3.3 μM final concentration)

Samples were incubated for 2 hrs at 37° C., boiled for 5 min., spun at 10,000 rpm for 3 min., diluted 1:10 and assayed as described above.

The quantitation of drug levels in the serum of rats following administration of the compound was done on a Micromedic 4/600 plus gamma counter using weighted liner regression analysis. Unknown samples were quantitated by comparing the number of bound counts remaining in the tube to those of a series of standards which contained varying amounts of drug spiked into whole rat blood, urine, or bile to a known concentration and assayed as described above.

EXAMPLE 4

Antibodies against a cleavage generated product for quantitation by immunoassays If the cleavage product to be detected by an RIA is larger than 20 amino acids, antibodies can be generated against the cleavage product by directly using the cleavage product to immunize rabbits by standard procedures. For smaller fragments, it is preferable to have the fragment conjugated to a carrier prior to immunization. Accordingly the cleavage product can be designed such that it carries a free cysteine at its N-terminus with a short spacer (Cys-Gly-Glu-Glu-) added to the fusion peptide. To accomplish this the free N-terminal cysteine was used to conjugate the peptide to porcine thyroglobulin while the spacer was introduced to avoid steric hinderance to the fusion peptide. The peptide was synthesized by solid phase methodology on an Applied Biosystems 430A synthesizer using their recommended protocol for double couple cycles for Boc-amino acids. After synthesis, each peptide was purified by preparative C18 reverse-phase chromatography using an appropriate linear gradient from 100% water (0.1% trifloroacetic acid) to a water/acetonitrile mixture (0.1% trifloroacetic acid). The pure peptides were lyophilized from water to yield a white powder. The peptides were analyzed for their expected molecular weight by FAB/MS, and each was a single symmetrical peak on analytical HPLC.

The peptide (12 mg) was conjugated to porcine thyroglobulin (20 mg) by using a well known methods. The procedure consists of activating the protein with the heterobifunctional cross-linking reagent, succinimidyl 4-(N-maleimidomethyl) cycloheane-1-carboxylate, followed by reaction with the sulfur of the cysteine of the peptide. Unreacted peptide and organic reagents were removed from the peptide/protein conjugate by extensive dialysis in Spectrapor 12000-14000 MW cutoff dialysis tubing.

Two adult female New Zealand White rabbits (#181 and 182) were used to generate antibodies against the cleavage product using the conjugated peptide. A solution of conjugated peptide (2 mg/ml) was made in phosphate buffered saline (PBS, 20 mM $NaH_2SO_4$, 150 mM NaCl, pH 7.5). An emulsion (2 ml) was then made with the peptide solution and complete Freund's adjuvant (1:1). Each rabbit was then injected with one half of the emulsion (1 ml, 1 mg conjugated peptide). All injections were interdermal and at multiple sites along the back and flank. Two booster injections (0.2 mg conjugated peptide) were prepared in incomplete Freund's adjuvant and injected interdermally at multiple sites. The injections were given at two week intervals. Blood was collected from each animal prior to immunization and six weeks after the initial injection. Subsequent bleedings were done at five week intervals. Sera was separated from the whole blood and stored at $-20°$ C. until use. The antisera can be used for developing quantitative immunoassays such as RIA and ELISA.

EXAMPLE 5

In another embodiment of the present invention, the TDP is made specific only for the HIV protease by eliminating renin specificity using modifications of the one or more amino acids in the $P_1'$ to $P_4'$ region. The preferred modified TDP's according to this invention are:

TDP-1)  $P_4$ = Pro = 2.22
$P_3$ = Phe = 1.92
$P_2$ = His = 1.14
$P_1$ = Leu = 3.66
$P_1'$ = Leu = 0.91
$P_2'$ = Val = 1.43
$P_3'$ = Tyr = 0.76
$P_4'$ = Ser = 1.89
$P_4 \times P_3 \times P_2 \times P_1 \times P_1' \times P_2' \times P_3' \times P_4' = RP = 33.24$
$h = \dfrac{33.24}{33.24 + 166} = 0.17$ TDP-2)  $P_4$ = Pro = 2.22
$P_3$ = Phe = 1.92
$P_2$ = His = 1.14
$P_1$ = Leu = 3.66
$P_1'$ = Leu = 0.91
$P_2'$ = Glu = 7.81
$P_3'$ = Ile = 1.44
$P_4'$ = Ser = 1.89
$P_4 \times P_3 \times P_2 \times P_1 \times P_1' \times P_2' \times P_3' \times P_4' = RP = 344$
$h = \dfrac{344}{344 + 166} = 0.67$ TDP-3)  $P_4$ = Pro = 2.22
$P_3$ = Phe = 1.92
$P_2$ = His = 1.14
$P_1$ = Leu = 3.66
$P_1'$ = Leu = 0.91
$P_2'$ = Glu = 7.81
$P_3'$ = Glu = 1.95
$P_4'$ = Ser = 1.89
$P_4 \times P_3 \times P_2 \times P_1 \times P_1' \times P_2' \times P_3' \times P_4' = RP = 465.83$
$h = \dfrac{465.83}{465.83 + 166} = 0.74$

EXAMPLE 6

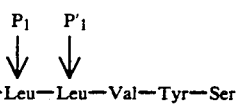

TDP-1) Asp—Arg—Val—Tyr—Ile—His—Pro—Phe—His—Leu—Leu—Val—Tyr—Ser

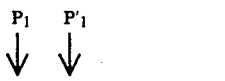

TDP-2) Asp—Arg—Val—Tyr—Ile—His—Pro—Phe—His—Leu—Leu—Glu—Ile—Ser

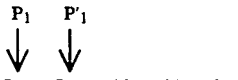

TDP-3) Asp—Arg—Val—Tyr—Ile—His—Pro—Phe—His—Leu—Leu—Glu—Glu—Ser

The probabilities for each of the TDP's are determined as follows:

In yet another embodiment of the present invention, the standard HIV diagnostic test can be performed using 1-2 μM of the modified tetradecapeptide substrates described in Example 5, 0.1-1 μg/ml active HIV protease, and 20 to 100-fold diluted sera from a patient. Samples can be incubated for 1-2 hrs at 37° C. and assayed for inhibition of product formation which can be measured by a radioimmunoassay for one of the products. The assay procedure is essentially the same as described in Example 1. Inhibition of HIV-1 protease activity is expressed in terms of nanograms of Ang I per ml per hr at 37° C.

TABLE I

| HIV-1 SPECIFICITY PARAMETERS | | | | | | | | |
|---|---|---|---|---|---|---|---|---|
| AMINO ACID | P4 | P3 | P2 | P1 | P1' | P2' | P3' | P4' |
| Asp | 1.75 | 0.88 | 0.11 | 0.11 | 0.11 | 0.11 | 0.88 | 1.75 |
| Asn | 0.14 | 0.14 | 3.41 | 2.27 | 0.14 | 0.14 | 0.57 | 1.14 |
| Glu | 0.78 | 3.12 | 1.17 | 0.39 | 1.17 | 7.81 | 1.95 | 0.39 |
| Gln | 0.64 | 3.85 | 0.16 | 0.16 | 0.16 | 3.85 | 0.16 | 0.64 |
| Ser | 1.89 | 0.38 | 0.76 | 0.09 | 0.38 | 0.09 | 1.52 | 1.89 |
| Gly | 1.28 | 0.64 | 0.08 | 0.96 | 0.32 | 0.08 | 0.64 | 0.96 |
| His | 1.14 | 0.50 | 1.14 | 0.50 | 0.50 | 0.50 | 0.50 | 0.50 |
| Arg | 1.56 | 1.56 | 0.13 | 0.13 | 1.56 | 0.13 | 2.08 | 0.52 |
| Thr | 0.86 | 1.72 | 1.72 | 0.11 | 0.86 | 0.43 | 2.16 | 1.29 |
| Ala | 2.01 | 0.57 | 1.15 | 0.57 | 1.72 | 0.57 | 1.15 | 0.57 |
| Pro | 2.22 | 0.56 | 0.14 | 0.14 | 2.78 | 0.14 | 0.14 | 2.22 |
| Tyr | 0.76 | 0.19 | 0.19 | 2.27 | 3.03 | 0.19 | 0.76 | 0.19 |
| Val | 0.36 | 0.09 | 3.21 | 0.09 | 1.07 | 1.43 | 0.71 | 0.09 |
| Met | 0.50 | 0.50 | 0.50 | 3.57 | 2.38 | 0.50 | 2.38 | 2.38 |
| Ile | 0.12 | 0.96 | 3.37 | 0.12 | 0.48 | 1.44 | 1.44 | 0.12 |
| Leu | 0.30 | 1.52 | 0.91 | 3.66 | 0.91 | 1.22 | 0.08 | 0.91 |
| Phe | 0.64 | 1.92 | 0.16 | 7.69 | 3.21 | 0.16 | 2.56 | 2.56 |
| Lys | 0.74 | 0.37 | 0.09 | 0.09 | 0.09 | 0.09 | 0.09 | 1.10 |
| Cys | 0.50 | 0.50 | 1.56 | 0.50 | 0.50 | 0.50 | 1.56 | 1.56 |
| Trp | 0.50 | 0.50 | 0.50 | 0.50 | 2.08 | 0.50 | 0.50 | 0.50 |

TABLE II

| HIV-2 SPECIFICITY PARAMETERS | | | | | | | | |
|---|---|---|---|---|---|---|---|---|
| AMINO ACID | P4 | P3 | P2 | P1 | P1' | P2' | P3' | P4' |
| Asp | 0.80 | 0.80 | 0.20 | 0.20 | 0.20 | 0.20 | 0.80 | 0.20 |
| Asn | 1.03 | 0.50 | 6.20 | 1.03 | 0.50 | 1.03 | 0.50 | 1.03 |
| Glu | 0.71 | 2.13 | 2.13 | 0.71 | 0.18 | 7.10 | 2.13 | 0.18 |
| Gln | 0.50 | 5.83 | 0.50 | 0.50 | 0.50 | 4.66 | 2.33 | 3.50 |
| Ser | 2.07 | 0.17 | 0.69 | 0.17 | 0.17 | 0.17 | 0.69 | 0.69 |
| Gly | 2.33 | 1.17 | 0.15 | 1.75 | 0.15 | 0.15 | 0.58 | 1.17 |
| His | 0.50 | 2.07 | 0.50 | 0.50 | 0.50 | 0.50 | 0.50 | 2.07 |
| Arg | 2.84 | 0.95 | 0.24 | 0.24 | 0.24 | 0.24 | 1.89 | 1.89 |
| Thr | 0.78 | 1.57 | 0.78 | 0.20 | 2.35 | 0.20 | 0.78 | 0.20 |
| Ala | 1.04 | 0.52 | 2.09 | 1.57 | 3.13 | 0.13 | 1.57 | 1.04 |
| Pro | 3.03 | 1.01 | 0.50 | 0.50 | 5.05 | 0.50 | 0.50 | 2.02 |
| Tyr | 2.75 | 0.50 | 0.50 | 2.75 | 1.38 | 0.50 | 0.50 | 0.50 |
| Val | 0.16 | 0.16 | 1.95 | 0.16 | 0.65 | 1.95 | 0.65 | 0.16 |
| Met | 0.50 | 0.50 | 0.50 | 6.49 | 4.33 | 0.50 | 2.16 | 2.16 |
| Ile | 0.22 | 0.87 | 2.62 | 0.22 | 0.22 | 1.75 | 0.87 | 0.22 |
| Leu | 0.14 | 1.11 | 0.55 | 3.88 | 0.55 | 1.11 | 1.66 | 0.55 |
| Phe | 0.50 | 2.33 | 0.50 | 2.33 | 3.50 | 0.50 | 1.17 | 4.66 |
| Lys | 0.17 | 0.17 | 0.17 | 0.17 | 0.17 | 0.17 | 0.17 | 1.34 |
| Cys | 0.50 | 0.50 | 0.50 | 0.50 | 0.50 | 0.50 | 2.84 | 0.50 |
| Trp | 0.50 | 0.50 | 0.50 | 0.50 | 0.50 | 0.50 | 0.50 | 0.50 |

I claim:

1. A method for identifying compounds which inhibit HIV protease activity comprising the steps of:
   a) combining a substrate, said HIV protease, anti-Ang I antibodies and a compound that is an HIV protease inhibitor candidate, said substrate comprising an HIV protease cleavage site, wherein said substrate does not bind with anti-Ang I antibodies and cleavage of said substrate by said HIV protease generates at least one reactive cleavage product which binds with anti-Ang I antibodies; and
   b) detecting the presence of said anti-Ang I antibodies that are bound with said reactive cleavage product, binding of anti-Ang I antibodies with a reactive cleavage product indicates that said HIV protease cleaved said substrate.

2. A method according to claim 1 wherein said HIV protease is HIV-1 protease.

3. A method according to claim 2 wherein said HIV protease cleavage site is selected from the group consisting of Pro-Phe-His-Leu-Leu-Val-Tyr-Ser, Pro-Phe-His-Leu-Leu-Glu-Ile-Ser and Pro-Phe-His-Leu-Leu-Glu-Glu-Ser.

4. A method according to claim 2 wherein said substrate is selected from the group consisting of: Asp-Arg-Val-Tyr-Ile-His-Pro-Phe-His-Leu-Leu-Val-Tyr-Ser; Asp-Arg-Val-Tyr-Ile-His-Pro-Phe-His-Leu-Leu-Glu-Ile-Ser; and Asp-Arg-Val-Tyr-Ile-His-Pro-Phe-His-Leu-Leu-Glu-Glu-Ser.

5. A method according to claim 1 wherein said anti-Ang I antibodies are immobilized upon a solid phase.

6. A method according to claim 5 wherein said anti-Ang I antibodies are immobilized upon the inner surface of a container such that said anti-Ang I antibodies will come into contact with material put into said container, and wherein said substrate, said HIV protease and said compound that is an HIV protease inhibitor candidate are combined in said container.

7. A method according to claim 6 comprising the additional steps of:
   a) adding a radiolabeled peptide to said container, wherein said radiolabeled peptide competes with said reactive cleavage product to bind with said anti-Ang I antibodies;
   b) removing unbound reactive cleavage product and unbound radiolabeled peptide from said container; and
   c) measuring amount of radiolabeled material is bound to said anti-Ang I antibodies.

8. A kit for identifying compounds that inhibit HIV protease activity, wherein said kit comprises a carton comprising:
   a) a container having anti-Ang I antibodies immobilized on its inner surface;
   b) a container comprising a substrate comprising an HIV protease cleavage site wherein said substrate does not bind to said anti-Ang I antibodies and wherein cleavage of said substrate by said HIV protease generates at least one reactive cleavage product which binds with said anti-Ang I antibodies; and,
   c) a container comprising HIV protease, said container comprising HIV protease being a different container than said container comprising said substrate.

9. A kit according to claim 8 wherein said HIV protease is HIV-1.

10. A kit according to claim 9 wherein said HIV protease cleavage site is an amino acid sequence is selected from the group consisting of Pro-Phe-His-Leu-Leu-Val-Tyr-Ser, Pro-Phe-His-Leu-Leu-Glu-Ile-Ser and Pro-Phe-His-Leu-Leu-Glu-Glu-Ser.

11. A kit according to claim 9 wherein said substrate is selected from the group consisting of: Asp-Arg-Val-Tyr-Ile-His-Pro-Phe-His-Leu-Leu-Val-Tyr-Ser; Asp-Arg-Val-Tyr-Ile-His-Pro-Phe-His-Leu-Leu-Glu-Ile-Ser; and Asp-Arg-Val-Tyr-Ile-His-Pro-Phe-His-Leu-Leu-Glu-Glu-Ser.

12. A method of detecting the presence of anti-HIV protease antibodies in a sample that is suspected of containing antibodies to HIV protease comprising the steps of:
   a) combining a substrate, HIV protease, anti-Ang I antibodies and a sample that is suspected of containing antibodies to HIV protease, said substrate comprising an HIV protease cleavage site wherein said substrate does not bind with anti-Ang I antibodies and cleavage of said substrate by said HIV protease generates at least one reactive cleavage product which binds with anti-Ang I antibodies; and b) detecting the presence of said anti-Ang I antibodies that are bound with said reactive cleavage product.

13. A method according to claim 12 wherein said anti-HIV protease antibodies are anti-HIV-1 antibodies and said HIV protease is HIV-1 protease.

14. A method according to claim 13 wherein said HIV protease cleavage site is selected from the group consisting of Pro-Phe-His-Leu-Leu-Val-Tyr-Ser, Pro-Phe-His-Leu-Leu-Glu-Ile-Ser and Pro-Phe-His-Leu-Leu-Glu-Glu-Ser.

15. A method according to claim 13 wherein said substrate is selected from the group consisting of: Asp-Arg-Val-Tyr-Ile-His-Pro-Phe-His-Leu-Leu-Val-Tyr-Ser; Asp-Arg-Val-Tyr-Ile-His-Pro-Phe-His-Leu-Leu-Glu-Ile-Ser; and Asp-Arg-Val-Tyr-Ile-His-Pro-Phe-His-Leu-Leu-Glu-Glu-Ser.

16. A method according to claim 12 wherein said anti-Ang I antibodies are immobilized upon a solid phase.

17. A method according to claim 16 wherein said anti-Ang I antibodies are immobilized upon the inner surface of a container such that said anti-Ang I antibodies will come into contact with material put into said container, and wherein said substrate, said HIV protease and said sample that is suspected of containing antibodies to HIV protease are combined in said container.

18. A method according to claim 17 comprising the additional steps of:

a) adding a radiolabeled peptide to said container, wherein said radiolabeled peptide competes with said reactive cleavage product to bind with said anti-Ang I antibodies;

b) removing unbound reactive cleavage product and unbound radiolabeled peptide from said container; and c) measuring amount of radiolabeled material is bound to said anti-Ang I antibodies.

19. A kit for detecting the presence of anti-HIV protease antibodies in a sample that is suspected of containing antibodies to HIV protease, wherein said kit comprises a carton comprising:

a) a container having anti-Ang I antibodies immobilized on its inner surface;

b) a container comprising a substrate comprising an HIV protease cleavage site wherein said substrate does not bind to said anti-Ang I antibodies and wherein cleavage of said substrate by said HIV protease generates at least one reactive cleavage product which binds with said anti-Ang I antibodies; and, c) a container comprising HIV protease, said container comprising HIV protease being a different container than said container comprising said substrate.

20. A kit according to claim 19 wherein said anti-HIV protease antibodies are anti-HIV-1 protease antibodies and said HIV protease is HIV-1 protease.

21. A kit according to claim 20 wherein said HIV protease cleavage site is selected from the group consisting of Pro-Phe-His-Leu-Leu-Val-Tyr-Ser, Pro-Phe-His-Leu-Leu-Glu-Ile-Ser and Pro-Phe-His-Leu-Leu-Glu-Glu-Ser.

22. A kit according to claim 19 wherein said substrate is selected from the group consisting of: Asp-Arg-Val-Tyr-Ile-His-Pro-Phe-His-Leu-Leu-Val-Tyr-Ser; Asp-Arg-Val-Tyr-Ile-His-Pro-Phe-His-Leu-Leu-Glu-Ile-Ser; and Asp-Arg-Val-Tyr-Ile-His-Pro-Phe-His-Leu-Leu-Glu-Glu-Ser.

* * * * *